(12) United States Patent
Richter et al.

(10) Patent No.: US 12,295,697 B2
(45) Date of Patent: May 13, 2025

(54) APPARATUS FOR MEASURING VITAL SIGNS

(71) Applicants: Wolfgang Richter, Vancouver (CA); Faranak Zadeh, Vancouver (CA)

(72) Inventors: Wolfgang Richter, Vancouver (CA); Faranak Zadeh, Vancouver (CA)

(73) Assignee: EPIC SEMICONDUCTOR INC

( * ) Notice: Subject to any disclaimer, the term of this patent is extended or adjusted under 35 U.S.C. 154(b) by 912 days.

(21) Appl. No.: 16/915,318

(22) Filed: Jun. 29, 2020

(65) Prior Publication Data

US 2021/0000348 A1 Jan. 7, 2021

Related U.S. Application Data

(60) Provisional application No. 62/869,183, filed on Jul. 1, 2019.

(51) Int. Cl.
| | |
|---|---|
| *A61B 5/277* | (2021.01) |
| *A61B 5/00* | (2006.01) |
| *A61B 5/02* | (2006.01) |
| *A61B 5/0205* | (2006.01) |
| *A61B 5/25* | (2021.01) |
| *A61B 5/304* | (2021.01) |
| *A61B 5/308* | (2021.01) |

(52) U.S. Cl.
CPC .............. *A61B 5/0031* (2013.01); *A61B 5/02* (2013.01); *A61B 5/02007* (2013.01); *A61B 5/02055* (2013.01); *A61B 5/25* (2021.01); *A61B 5/277* (2021.01); *A61B 5/304* (2021.01); *A61B 5/308* (2021.01); *A61B 2560/0214* (2013.01); *A61B 2562/0214* (2013.01); *A61B 2562/182* (2013.01)

(58) Field of Classification Search
None
See application file for complete search history.

(56) References Cited

U.S. PATENT DOCUMENTS

| | | | | |
|---|---|---|---|---|
| 4,715,384 A | * | 12/1987 | Tabata | A61B 5/0245 600/523 |
| 9,369,824 B2 | | 6/2016 | Richter et al. | |

(Continued)

*Primary Examiner* — Meredith Weare

(57) ABSTRACT

Disclosed is an apparatus for battery-free measuring vital signs of a user from a single position near the user influenced by an alternating electric field provided by an electronic device. The apparatus includes a first electronic circuitry, a second electronic circuitry stacked to the first electronic circuitry, an instrumentation amplifier for amplifying the signals, an analog/digital converting logic circuit for generating digitized information, and a communication unit for communicating the digitized information. The first electronic circuitry includes a first electrode for receiving vital signals (acoustic, mechanical, electrical signals) from the user's body, a first shield unit for shielding the first electrode from electrical influences and influenced by the alternating electric field provided by the electronic device, a first rectifier for harvesting and rectifying the received alternating electric field from the first shield unit, further the first rectifier provides DC energy, a first buffer stores the DC energy and provides differential voltages, a first programmable operational amplifier amplifies the amplitude of the received vital signs powered by the received differential voltage from the first buffer.

17 Claims, 8 Drawing Sheets

(56) References Cited

U.S. PATENT DOCUMENTS

| | | | |
|---|---|---|---|
| 9,509,178 B2 | 11/2016 | Richter et al. | |
| 2005/0070778 A1* | 3/2005 | Lackey | A61B 5/4875 |
| | | | 600/366 |
| 2011/0213274 A1* | 9/2011 | Telfort | A61B 7/04 |
| | | | 600/586 |
| 2012/0004523 A1* | 1/2012 | Richter | A61B 5/25 |
| | | | 600/509 |
| 2016/0287128 A1* | 10/2016 | Jain | A61B 5/327 |
| 2020/0001175 A1 | 1/2020 | Richter et al. | |

* cited by examiner

APPARATUS FOR MEASURING VITAL SIGNS

CROSS-REFERENCE TO RELATED APPLICATIONS

The present application claims the benefit of U.S. Provisional Application No. 62/869,183, filed Jul. 1, 2019, which is incorporated by reference herein in its entirety.

BACKGROUND OF THE INVENTION

1. Field of the Invention

The present invention generally relates to an apparatus for measuring vital signs and more particularly relates to measuring a number of different vital signs of a user influenced by an alternating electric field with an apparatus positioned near to the user.

2. Description of Related Art

Today's wearable computing is often combined with electronic circuits for measuring fitness, wellness, and health status. While the art knows several methods to measure vital signs, it always requires the direct involvement of the user. This may interrupt ongoing activities or more important critical vital signs that may not be noticed at the right time.

Also, the art teaches applicable electronic patches, attached to a user's skin, that measure certain vital signs and transfer the resulting information wirelessly to computers or networks. Such patches are often battery operated and/or activated utilizing electromagnetic waves.

Various devices are known in the art such as controller/generator to provide an alternating electric field. U.S. Pat. No. 9,509,178 and US20200001175A1 disclose a hub unit for generating an alternating electric field, and U.S. Pat. No. 9,369,824B2 discloses a computing device for generating a modulated alternating electric field.

To conserve energy in battery-operated sensing systems, such have to be in a "sleep mode" most of the time, while electromagnetic activated ones force the user to perform repeating action (e.g. RFID/NFC readout) by placing a smart device near to the patch.

A number of devices designed for monitoring vital signs are known. In a hospital setting, where a patient's heart rate and function are being monitored, it is usual to record a continuous electrocardiogram (EKG or ECG) of the patient. This is performed by attaching a number of wired electrodes to various points of the patient's chest and back region, to measure the rhythmic electrical activity of the heart.

An EKG hookup tends to be uncomfortable and confining over extended periods and requires a trained medical professional to apply the electrodes properly and to operate the device. For example, during sleep, the electrodes can come off the patient and cause a false alarm. The cost and inconvenience of EKG monitoring make it impractical for many health-monitoring settings, such as non-critical hospital patients, infant-, mobile-, or elder care monitoring.

Therefore, there is a need for a (preferably battery-free) apparatus for permanent uninterrupted measuring of various vital signs of a user in the form of an electronic tattoo or attachable flexible patch which e.g. works through the fabric of clothes or furniture. The apparatus should communicate with networks and or smart devices. The apparatus should further have related electronic circuitry attached to a flexible carrier which acts as a shield against electromagnetic influence, an active electrode, and/or a kind of contact microphone.

SUMMARY OF THE INVENTION

In accordance with the teachings of the present invention, an apparatus for measuring vital signs of a user influenced by an alternating electric field provided by an electronic device is provided.

An object of the present invention introduces an apparatus which includes a first electronic circuitry, a second electronic circuitry stacked to the first electronic circuitry, an instrumentation amplifier for amplifying the vital signals, an analog/digital converting logic circuit for generating digitized information, and a communication unit for wirelessly communicating the digitized information.

The first electronic circuitry includes a first electrode for receiving vital signs from the user's body, a first shield unit for shielding the first electrode from electrical influences, a first rectifier for harvesting and rectifying the received alternating electric field for providing a DC energy, a first buffer for storing the DC energy and provides differential voltages, and a first programmable operational amplifier which amplifies the amplitude of the received vital signs powered by the received differential voltage from the first buffer.

The second electronic circuitry has identical components as of the first electronic circuitry. Further, an instrumentation amplifier receives the amplified signals from the first programmable operational amplifier and the second programmable operational amplifier to suppress electrical noise/influence. The instrumentation amplifier creates an amplified value analog to the vital sign.

The analog/digital converting logic circuit generates digitized information from the received amplified vital signs from the instrumentation amplifier. The communication unit communicates the digitized information received from the analog/digital converting logic circuit over a communication network.

Another object of the present invention is to provide the apparatus with a first impedance filter and a second impedance filter to filter vital signals from the received signals. Further, the apparatus includes a first electronic switch and a second electronic switch to discharge static charges.

Another object of the present invention is to provide the apparatus with a first shield driver and a second shield driver to drive the received vital signs back to the shield unit to suppress or cancel influential noise. Further, the first electrode and the second electrode are piezo coated for receiving electrical, mechanical, and acoustic signals from the user.

Another object of the present invention is to provide the apparatus wherein the electronic device performs impedance spectroscopic analysis from the alternating electric field sweeps to measure bio-resonances. Further, the apparatus is configurable within an implantable device and/or medical device such as a catheter for clog detection in blood vessels, and/or as a thermometer to measure temperatures of (or inside) the body.

BRIEF DESCRIPTION OF DRAWINGS

The annexed drawings, which are not necessarily to scale, show various aspects of the inventions in which similar reference numerals are used to indicate the same or similar parts in the various views.

DETAILED DESCRIPTION OF DRAWINGS

It is believed that the invention will be better understood from a consideration of the description of exemplary embodiments in conjunction with drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

Figure 1:
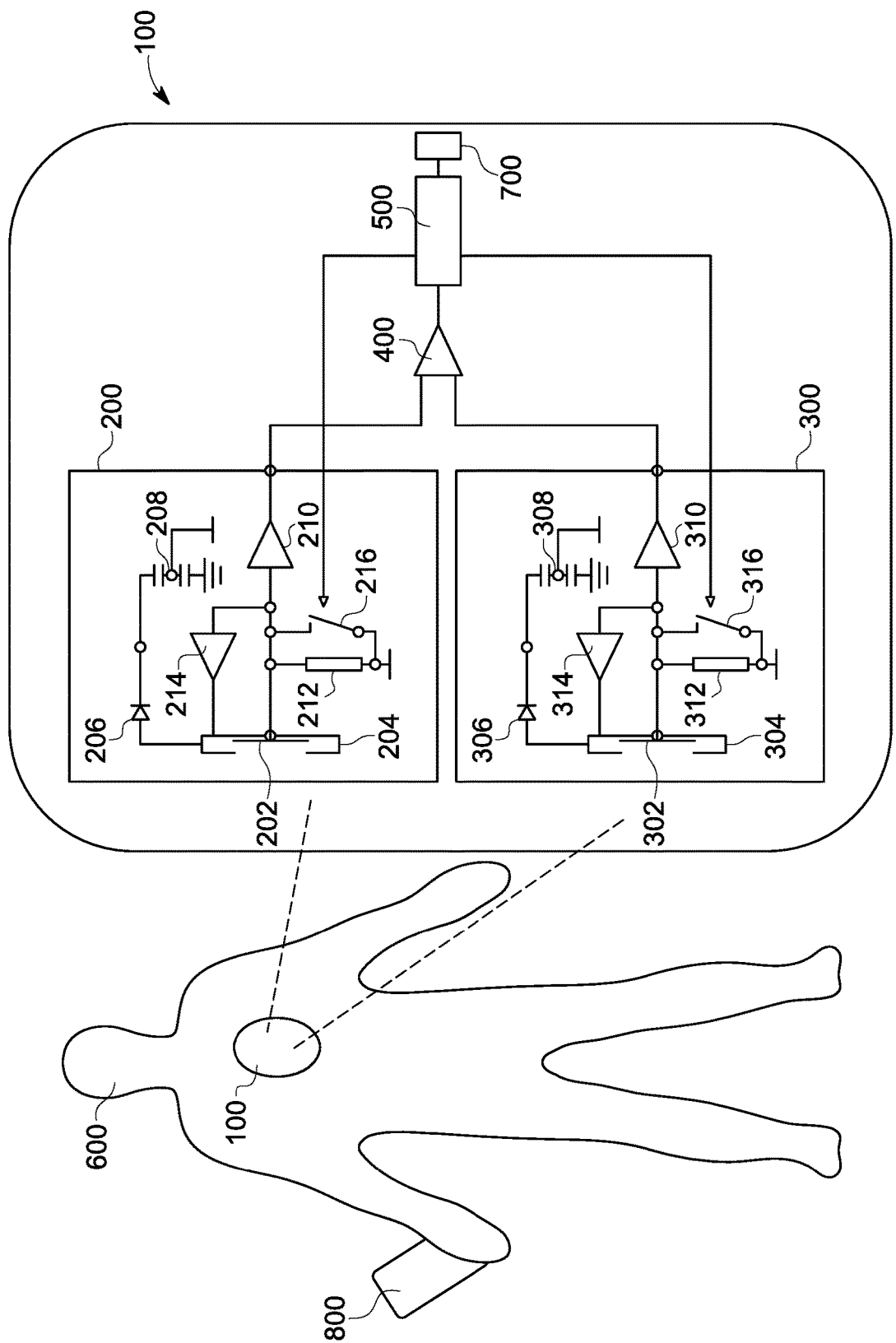
FIG. 1 illustrates a schematic diagram of the apparatus attached to a user in accordance with a preferred embodiment of the present invention.

FIG. 1 illustrates a schematic diagram of the apparatus 100 attached to a user 600 in accordance with a preferred embodiment of the present invention. The apparatus 100 measures vital signs of the user 600 influenced by an alternating electric field provided by an electronic device 800.

The apparatus 100 includes a first electronic circuitry 200, a second electronic circuitry 300, an instrumentation amplifier 400, an analog/digital converting logic circuit 500 and a communication unit 700. Examples of the user 600 include but not limited to organisms like animals, plants, and humans to get information about their physical and/or mental state.

The first electronic circuitry 200 includes a first electrode 202, a first shield unit 204, a first rectifier 206, a first buffer 208 and a first programmable operational amplifier 210. The first electrode 202 receives vital signs from the user's 600 body. Examples of the vital signs include but not limited to heartbeat, breathing, acoustic signals, sneezing, coughing, vomiting, joint movements, impacts, rhythm, body movements, ways of how a user walks, drives, works, speaks, or acts, body temperature, sweat, etc.

The first field shield unit 204 shields the first electrode 202 from electrical influences. Further, the first shield unit 204 is influenced by the alternating electric field provided by the electronic device 800. The electronic device 800 generates and deploys an alternating electric field as a resonating oscillation. Examples of the first field shield unit 204 include but not limited to metallic or conductive sheet, foil or printing. Examples of the electrical influence include but not limited to static pulses, electrical noise, EMG waves, electro-smog.

The first rectifier 206 harvests and rectifies the received alternating electric field from the first field shield unit 204. Further, the first rectifier 206 provides DC energy. This leads to battery-free "always-on" (no sleep modes) operation of the first electronic circuitry 200. Examples of the rectifier 206 include but not limited to (ideal) diodes, ESD circuits, Graetz bridges, phase switches, MOS/BJT transistors etc.

The first buffer 208 stores DC energy and further provides differential voltages (e.g. +/−5V). Examples of the first buffer 208 include but not limited to capacitors, gold caps, dielectric material (e.g. polymer) between conductive surfaces, (printed) accumulators, etc. The first buffer 208 stores the electrical energy and provides a virtual ground.

The first programmable operational amplifier 210 amplifies the amplitude of the received vital signals powered by the received differential voltage from the first buffer 208. Examples of the first programmable operational amplifier 210 include but not limited to Field-Effect Transistors (FET), Operational Amplifier (OPamps), Programmable-Gain Amplifier (PGAs), Voltage Controlled Amplifier (VCAs), Digital Controlled Amplifiers (DCAs), switched capacitor OPs, analog multipliers, etc.

The second electronic circuitry 300 is stacked to the first electronic circuitry 200. The second electronic circuitry 300 includes a second electrode 302, a second shield unit 304, a second rectifier 306, a second buffer 308 and a second programmable operational amplifier (PGA) 310. The second electronic circuitry 300 works identical to the first electronic circuitry 200 which is explained in paragraph [0027] to paragraph [0031].

The distance between the first electrode 202 and the second electrode 302 creates a delta ratio from the user's 600 received vital signs, as well as a small delta ratio from potential electromagnetic influence (e.g. 60 Hz AC hum). Both PGA (210,310) outputs are connected to the instrumentation amplifier (INA) 400. Its high common-mode rejection ratio (CMRR) suppresses the electrical noise and connects a cleaner vital sign to the analog/digital converting logic circuit 500.

As the vital signs propagate through the user's human body and over the skin (dermis) the arrangement allows detecting e.g. human heartbeat almost everywhere on the body with a single apparatus 100, even through fabrics, plastic, fur or leather, or other non-conductive material, e.g. in or on clothes, shoes, helmets, glasses, gloves, machine parts, protection devices, products, furniture etc.

The instrumentation amplifier 400 receives the amplified vital signals from the first programmable operational amplifier 210 and the second programmable operational amplifier 310 to suppress the electrical noise/influences (e.g. 50/60 cycle mains hum). Further, the instrumentation amplifier 400 creates an amplified analog value representing the vital signs. Examples of the instrumentation amplifier 400 include but not limited to differential OPamps, INAs, analog multipliers, etc.

The analog/digital converting logic circuit 500 generates digitized information from the received amplified vital signs values from the instrumentation amplifier 400. Examples of the analog/digital converting logic circuit 500 include but not limited to SAR, ADCs (e.g. Wilkinson/Delta-Sigma/Slope etc.), pulse interval converter (VPIC), VCOs, PLL, MCUs, SOCs, etc.

The communication unit 700 communicates the digitized information received from the analog/digital converting logic circuit 500 over a communication network. Examples of the communication unit 700 include but not limited to Wi-Fi, internet, NFC, Bluetooth, LAN, LoRa, 5 G, and other similar wired and (preferably) wireless communication devices.

The instrumentation amplifier 400, the analog/digital converting logic circuit 500 and the communication unit 700 are powered by the DC energy from the first buffer 208. The analog/digital converting logic circuit 500 further modulates the alternating electric field with the converted A/D information which allows wireless wire-free non-magnetic operation of the apparatus 100.

The user's body produces various vital signals such as electro-myograms from muscles and the heart, acoustic sounds from mouth, nose, heart, and lungs, biomechanical waves from movements or tremor. The vital signals propagate over the human skin as waves. Other vital signals may be derived from body liquids, like blood, sweat, tears, urine, tissue, fats etc., as they may cause changes in the electrical impedance, influencing the wave propagation.

The apparatus 100 measures vital signs from the vital signals and may be attached or placed near the user's 600 body. The apparatus 100 is able to measure the vital signs of the user 600 through fabrics, plastics, leather, footwear etc. The apparatus 100 is wirelessly powered by and communicates over the alternating electric field influencing the human body, thus no batteries are required for continuous ("always-on") operation.

In another embodiment of the present invention, the first electronic circuitry 200 further includes a first impedance filter 212 to filter vital signs from the received vital signals, a first shield driver 214 to drive the received vital signs back to the first shield unit 204 to cancel influential noise, and a first electronic switch 216. The first programmable operational amplifier (OP PGA) 210 is biased over the first impedance filter 212 against the virtual ground. Further, the first electronic switch 216 discharges the PGA input on demand e.g. after a sampling event.

In another embodiment of the present invention, the second electronic circuitry 300 further includes a second impedance filter 312 to selectively filter vital signals from the signals received from the user's 600 body, a second shield driver 314 to drive the received vital signs back to the second shield unit 304 and to cancel influential noise, and a second electronic switch 316.

Further, the analog/digital converting logic circuit 500 modulates the impedance of the first impedance filter 212, the second impedance filter 312, the first shield driver 214 and the second shield driver 314 with the digitized information via the first electronic switch 216 and the second electronic switch 316. This affects the filter characteristics and modulates the alternating electric field with the digitized information. Examples of the first impedance filter 212 and the second impedance filter 312 include but not limited to L-R-C combinations, coils, resistors, capacitors, switching filter arrangements, etc. Examples of the first shield driver 214 and the second shield 314 includes but not limited to (FET) OPamps, transistor subcircuits.

The modulated digitized information propagates to the electronic device 800 (preferably over the user's skin) via the alternating electric field. The electronic device 800 converts the resulting changes in its impedance to values representing the vital signs. Examples of the electronic device 800 include but not limited to a smartphone, a controller, a computer etc.

In an exemplary embodiment of the present invention, the piezo coated first electrode 202 and the second electrode 302 receive electrical (e.g. ECG) and mechanical signals (e.g. BCG, pulse wave, blood pressure) from the user's 600 (e.g. heart) and connect them to the first programmable operational amplifier 210 and to the second programmable operational amplifier 310, as well as to the first shield driver 214 and the second shield driver 314 which drive the signal back to the first shield unit 204 and the second shield unit 304. Further, the piezo coating can be applied in the form of concentric rings.

Figure 2:
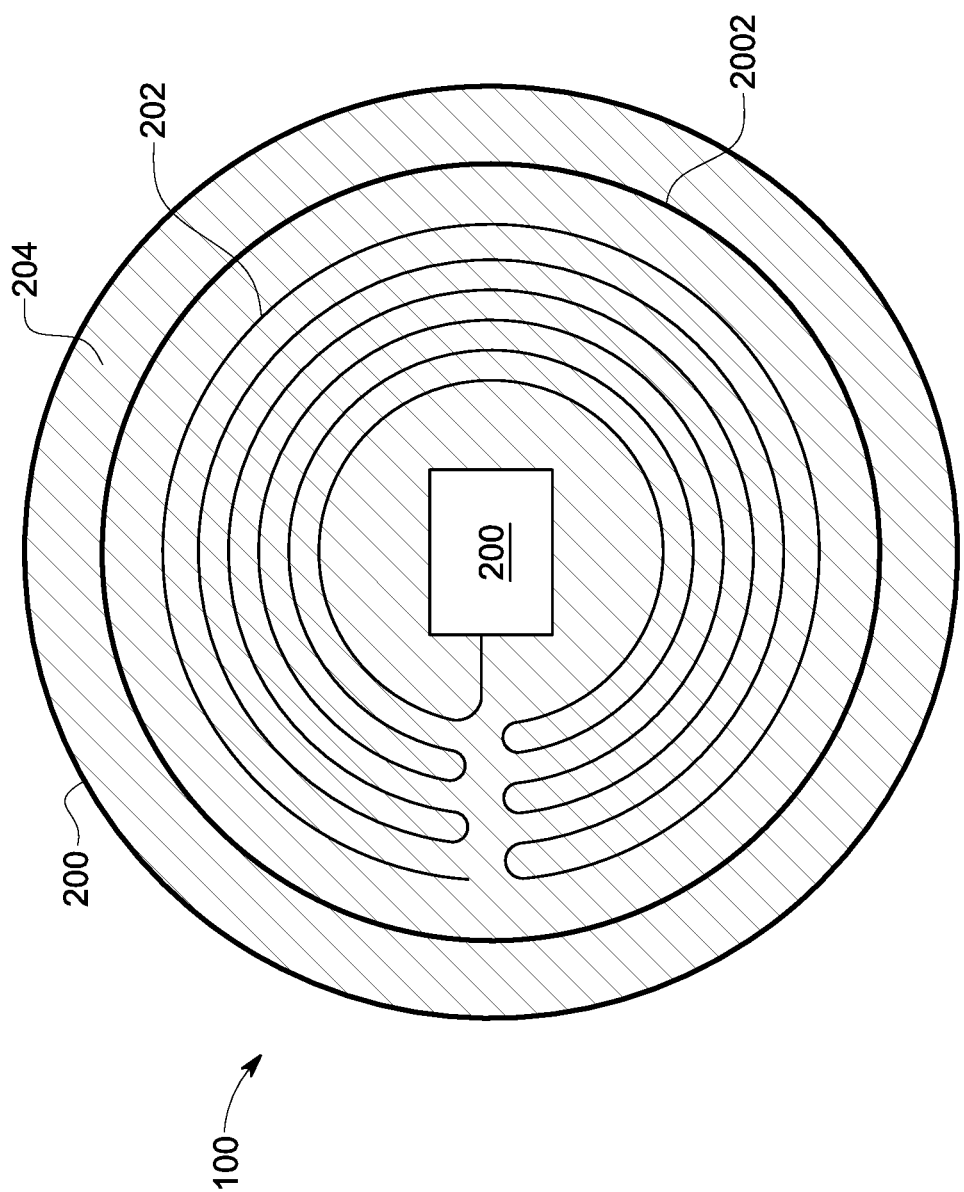
FIG. 2 illustrates a sectional view of the apparatus for measuring vital signs in accordance with an embodiment of the present invention.

FIG. 2 illustrates a sectional view of the apparatus 100 for measuring vital signs in accordance with an embodiment of the present invention. The first electronic circuitry 200 is positioned in the center. The first electrode 202 surrounds the first electronic circuitry 200. The first electrode 202 has bifilar windings to reject magnetic influence (e.g. AC hum). The bifilar winding suppresses electromagnetic influence (e.g. 60 Hz hum) to a certain degree. The apparatus 100 may further be attached to a becoming mother's belly to monitor a fetus (not shown).

Further, the first electrode 202 is piezo coated 2002 (usable as sensor or actor) to serve as a contact microphone (e.g. stethoscope) and is able to receive acoustic signals and mechanical waves from the user's body 600. Examples of the signals include but not limited to heartbeat, breathing, coughing, vomiting, joint movements, impacts, rhythm, body movements, ways of how a user walks, drives, works or acts, speech etc. The first electrode 202 and the first shield unit 204 may be provided with non-magnetic preferably flexible conductive materials (e.g. anti-static rubber or polymer).

The piezo coating 2002 causes piezo effects (e.g. vibrations) that may be used for wound healing, nerve stimulation, or drug delivery on demand. The first electronic circuitry 200 may be used to detect or identify implants or the piezo coating 2002 allows the doctors/surgeons to locate a route in the user's 600 (patient's) body for delivery of drugs, or detecting clogs, based on acoustic/biomechanical signals.

The first shield unit 204 protects against electromagnetic waves (e.g. electro-smog). Besides receiving bio-acoustic signals, the piezo coating 2002 may emit or receive ultrasonic pulses. Layers of piezo coating may create intensive beat-patterns of a wide frequency range for different purposes (e.g. stimulation, signalling, speakers, resonators, etc.).

The user's 600 vital signals are measured through fabrics, plastic, leather etc. worn by or near to the user. Further, the body electrode 202 has bifilar windings that reject magnetic influence (e.g. AC mains hum). Furthermore, the shield unit 204 is double-sided, building an outer ring on the front while covering the full rear side.

Figure 3:
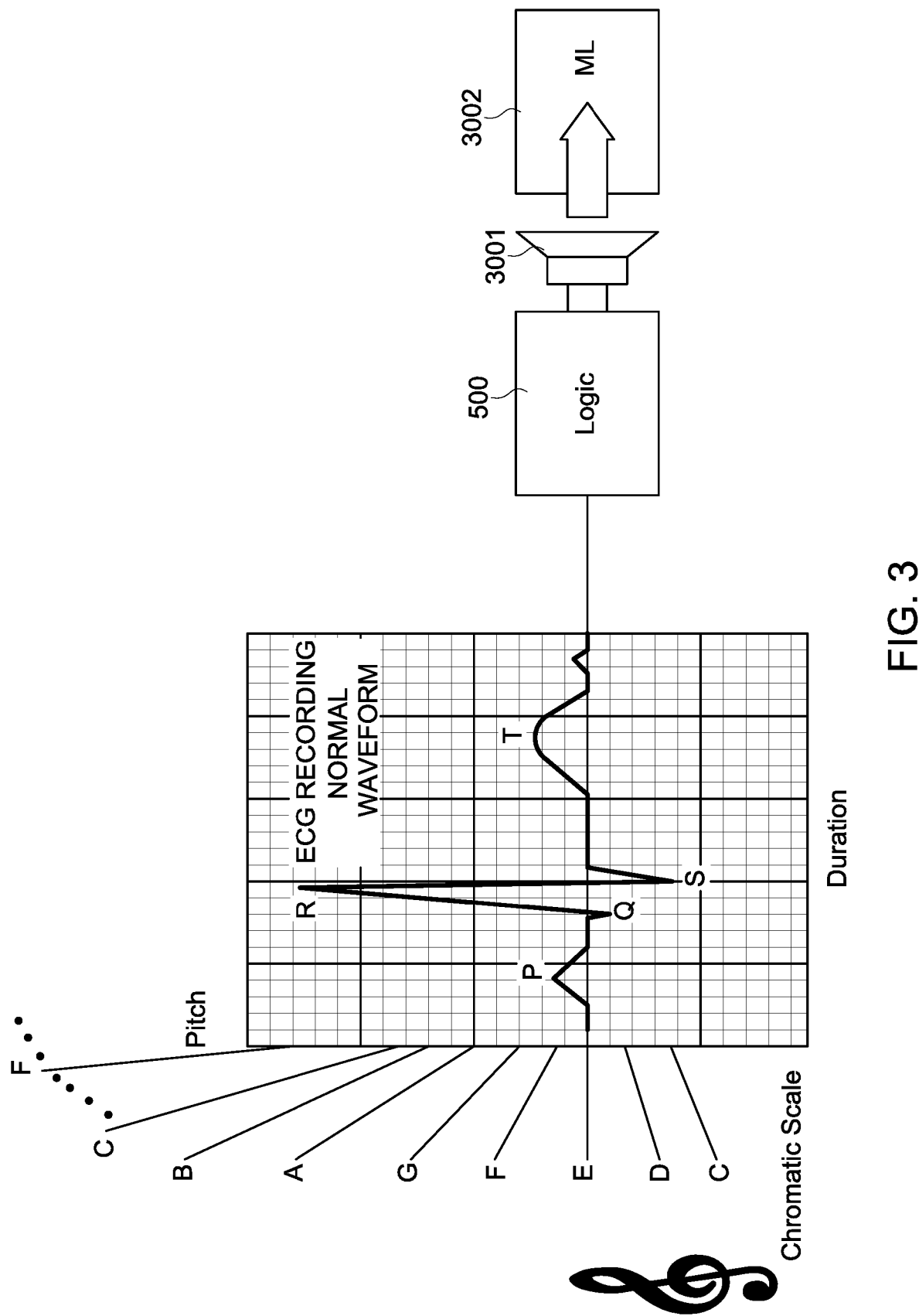
FIG. 3 illustrates a schematic diagram to convert vital signs into a melody in accordance with another preferred embodiment of the present invention.

FIG. 3 illustrates a schematic diagram to convert vital signs into a melody in accordance with another preferred embodiment of the present invention. For exemplary purposes, the ECG or other vital signals are turned into a melody. The received ECG signal changes the pitch and duration of a sound source 3001 (e.g. VCO) due to converting and processing of the first (active) electrode 202 (shown in FIG. 1). A machine learning algorithm 3002 may be instructed to train and arrange perceptrons to identify users (or other living organisms) on specific vital signals.

For exemplary purposes, a car seat charged with the apparatus 100 (shown in FIG. 1), in the form of a flexible foil inside, adjusts automatically if a driver is identified. Further, said apparatus 100 (shown in FIG. 1) continuously monitors the awareness and wellness of the driver or passengers contactless and battery-free. The first electronic circuitry 200 and the second electronic circuitry 300 (shown in FIG. 1) are provided as a silicon die or as printable electronics (when available) attached to a preferably flexible carrier sheet (e.g. rubber or polymer).

The analog/digital converting logic circuit 500 may be a controller, which generates, deploys, and modulates an alternating electric field with identification and vital signs data, yet it also receives energy from the active electrodes, which they harvest from external sources. The analog/digital converting logic circuit 500 receives and decodes commands modulated into the alternating electric field e.g. to set the gain in the invention related programmable amplifiers (or shield drivers). The analog/digital converting logic circuit 500 communicates with other controllers, computers, or networks e.g. via the communication unit 700 (shown in FIG. 1).

Wires, cables, and connectors are costly, need complex assembly and are failure-sensitive. The invention doesn't require any of those, therefore it apparently saves more time, assembly efforts and money than it cost. To reduce the investment further, the first electronic circuitry (200, shown in FIG. 1) and the second electronic circuitry (300, shown in FIG. 1) may be provided as an integrated circuit (e.g. silicon, GaN, etc.) die (or as printable electronics when available).

Figure 4A:
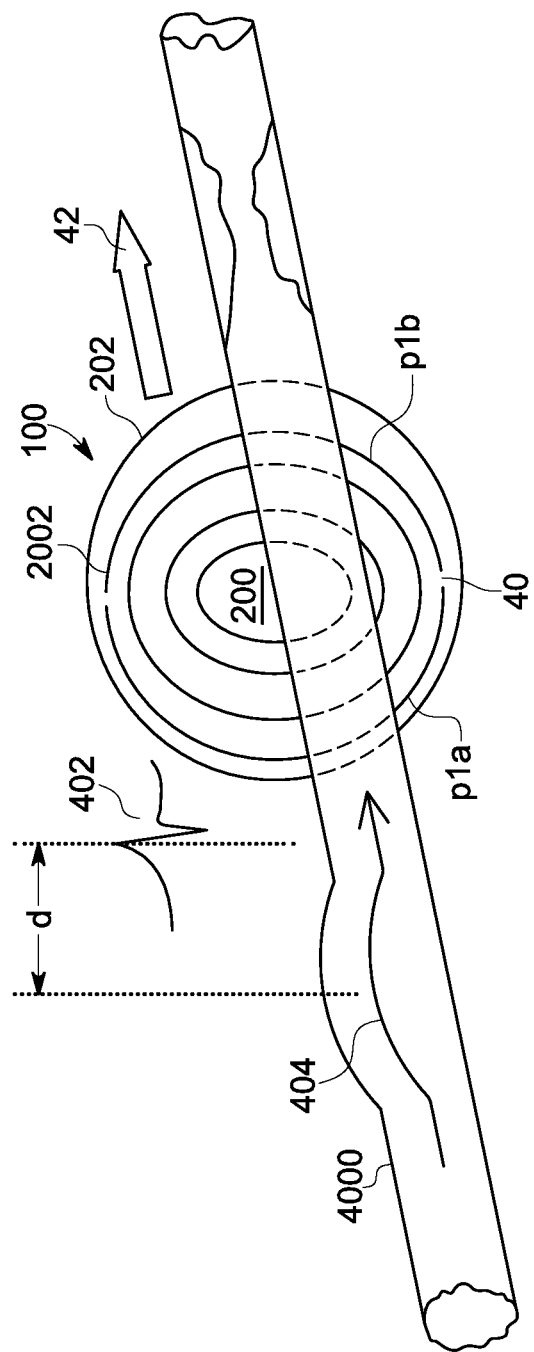
FIG. 4A shows a schematic view of the apparatus detecting electrical and mechanical signals from arteries in an exemplary embodiment of the present invention.

FIG. 4A shows a schematic view of the apparatus 100 detecting electrical signals from arteries 4000 in an exemplary embodiment of the present invention. The first electrode 202 coated with piezo rings 2002 couples capacitively with the first electronic circuitry 200. Assuming all body signals propagate through (and over) the body, it is apparent that electrical signals 402 propagate over veins and arteries as well as the mechanical pulse waves 404 do.

Electrical signals 402 from the heart (ECG) are much quicker than the resulting mechanical pulse waves 404, therefore they reach the apparatus 100 first early followed by a pulse wave as shown by the interval 'd'. The pulse waves pass through the piezo coating rings 2002 which results in electrical pulses that are capacitively induced into the first electrode 202.

The concentric coating p1a and p1b are the same piezo ring, yet interrupted (40) to detect the direction of the pulse-wave, it's amplitude and its speed. The invention-related electrode may be moved as shown by arrow 42 to scan an artery (blood vessel) from the outside to measure a variation in blood speed and blood pressure, which helps to detect diseases such as clogs 4002.

Figure 4B:
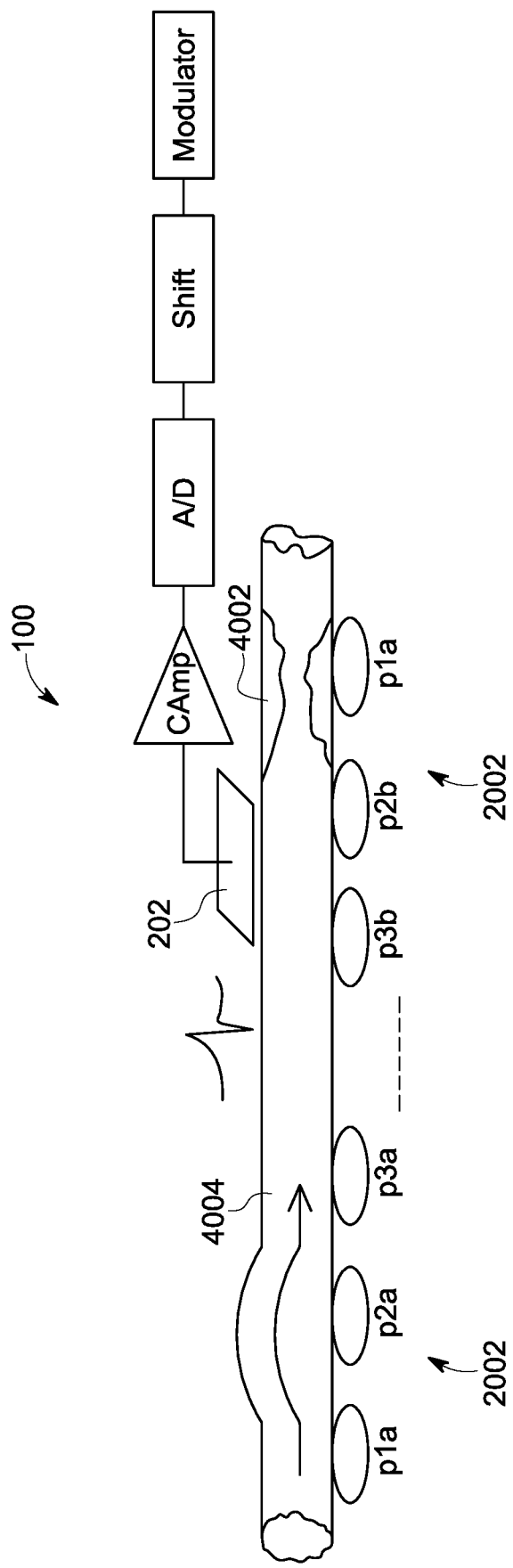
FIG. 4B shows a schematic view (cut) of the apparatus for demonstrating the working principle in accordance with another exemplary embodiment of the present invention.

FIG. 4B shows a schematic view (cut) of the apparatus 100 for demonstrating the working principle in another embodiment of the present invention. The ECG signal propagates along the arteria and is received by the first electrode 202, while the resulting pulse wave passes the piezo rings (p1, p2, p3) one after the other, which allows measuring the speed of the wave, as well as its amplitude and direction, which represents the blood pressure (pulse-tonography).

It would be readily apparent to those skilled in the art that the apparatus 100 may be attached to various objects such as door handles, pens, medical devices, remote controls, personalized smart devices 800 or consumer goods to identify users on their intrinsic heart signals without deviating from the scope of the present invention.

Concentric piezo rings for pulse wave measurement are a good example of printable electronics (PE). The concentric embodiments allow an orientation-free measurement of a pulse wave 404. If the direction of the pulse wave is required in certain analytics, the rings may be interrupted, as shown (FIG. 4a, 40). In parts, this also helps to determine the angle of the arteria.

In an embodiment, the apparatus 100 is able to detect blood pressure and speed, further it may also be used to detect clogged 4002 arteries 4004. Due to the so-called Bernoulli effect on liquids flowing in narrowing tubes, the pressure is decreasing while the speed is increasing. This happens in a vein or artery 4004 because of cholesterol clogs 4002 inside. The invention would also work in implants or catheters.

Figure 5:
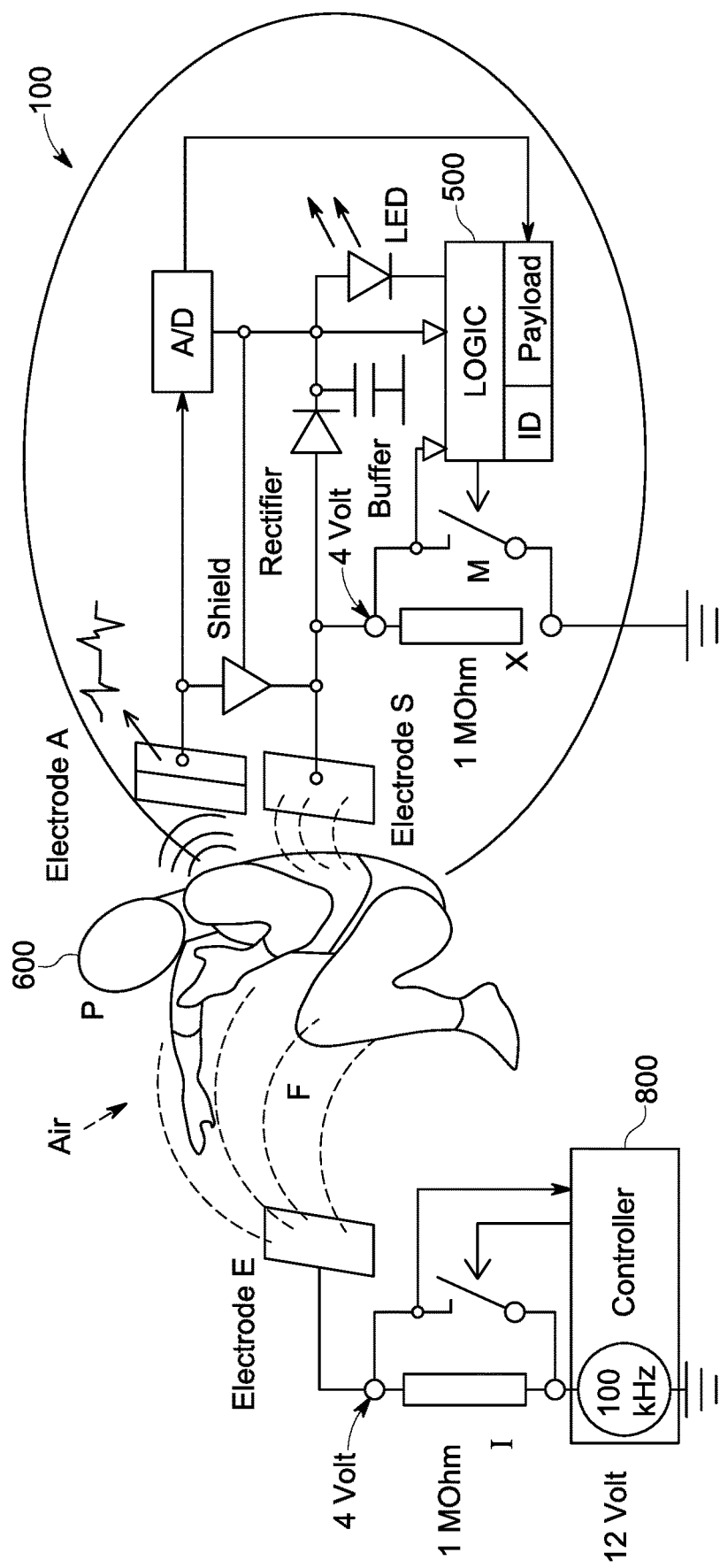
FIG. 5 illustrates a schematic diagram of the working principle of the apparatus in accordance with the preferred embodiment of the present invention.

FIG. 5 illustrates a schematic diagram of the working principle of the apparatus 100 in accordance with the preferred embodiment of the present invention. The electronic device 800 contains and operates a generator that outputs a certain frequency e.g. 100 kHz over an impedance (I) and an electrode (E) where it emits as an alternating electric field (F).

A user (person P) near the electrode (E) is influenced by the alternating electric field (F). The invention related surface electrode (a combination of A (202) & S (204)) explained in FIGS. 1 & 2 is also near the said person (P) and therefore also influenced by the alternating electric field (F). The alternating electric field energy is rectified and buffered to create a (preferable differential) DC voltage to operate the electronic components inside the apparatus 100.

The field's frequency is triggered to generate a clock to operate the digital logic parts of the apparatus 100. The analog/digital converting logic circuit 500 contains means e.g. counters and registers to shift out a unique identification number (ID) and a digitized value (Payload) which may represent the measured vital signs. For simplification, the electronic device 800 includes a modulator switch (parallel to impedance I) which changes the impedance (I) to communicate, e.g. send commands to the analog/digital converting logic circuit 500. Said switch may be realized e.g. using a MOS transistor.

The modulation causes voltage changes on the impedance (X) of the apparatus' 100 controller circuit which can be detected, interpreted, and processed by the logic unit 500. The electronic device (800 as shown in FIG. 1) generally contains a controller (hereinafter referred to as controller 800), a generator, a switch (for modulation of data) and an electrode to emit an alternating electric field over a (preferably resonating) impedance (I).

Figure 6:
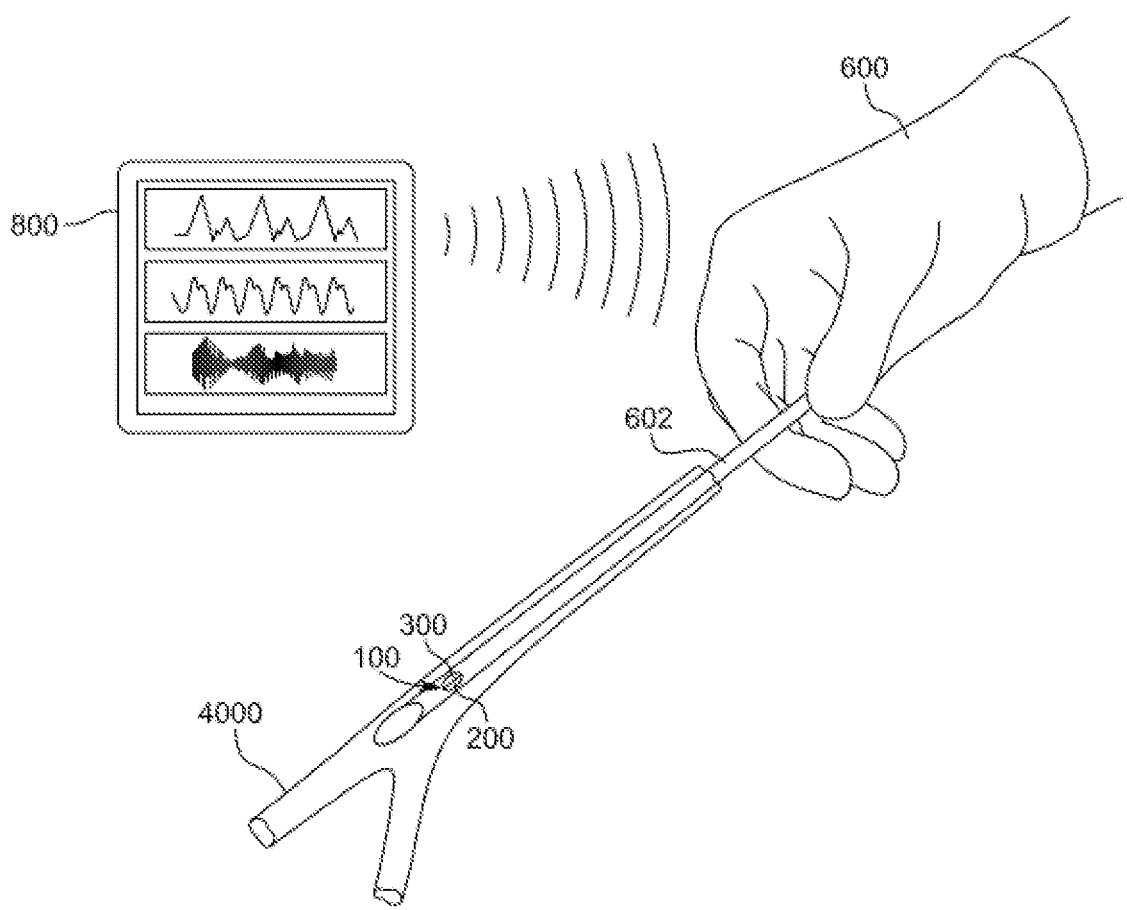
FIG. 6 shows a schematic view of the apparatus attached to a medical device for detecting electrical and mechanical signals from arteries in an exemplary embodiment of the present invention.

The controller 800 extracts data from the received modulation provided by the logic unit 500 operating the modulation switch (M) and further propagating via the alternating electric field, and further processes and communicates the processed data via communication networks. The controller 800 sends data into the apparatus 100 by modulating its impedance (I) and/or its frequency or duty cycle. The controller 800 and the apparatus 100 may be separated from each other and mounted e.g. in a car seat. A person (P) seated on it bridges the alternating electric field (F) emitted by the controller's electrode (E) over his/her body and received by the apparatus which filters out vital signs as described. p FIG. 6 shows a schematic view of the apparatus 100 attached to a medical device 602 for detecting electrical and mechanical signals from arteries 4000 in an exemplary embodiment of the present invention. In an embodiment, the medical device 602 is a catheter. The apparatus 100 are configured within a catheter 602 for clogs detection in blood vessels (same as arteries 4000). The second electronic circuitry 300 is stacked to the first electronic circuitry 200.

Figure 7:
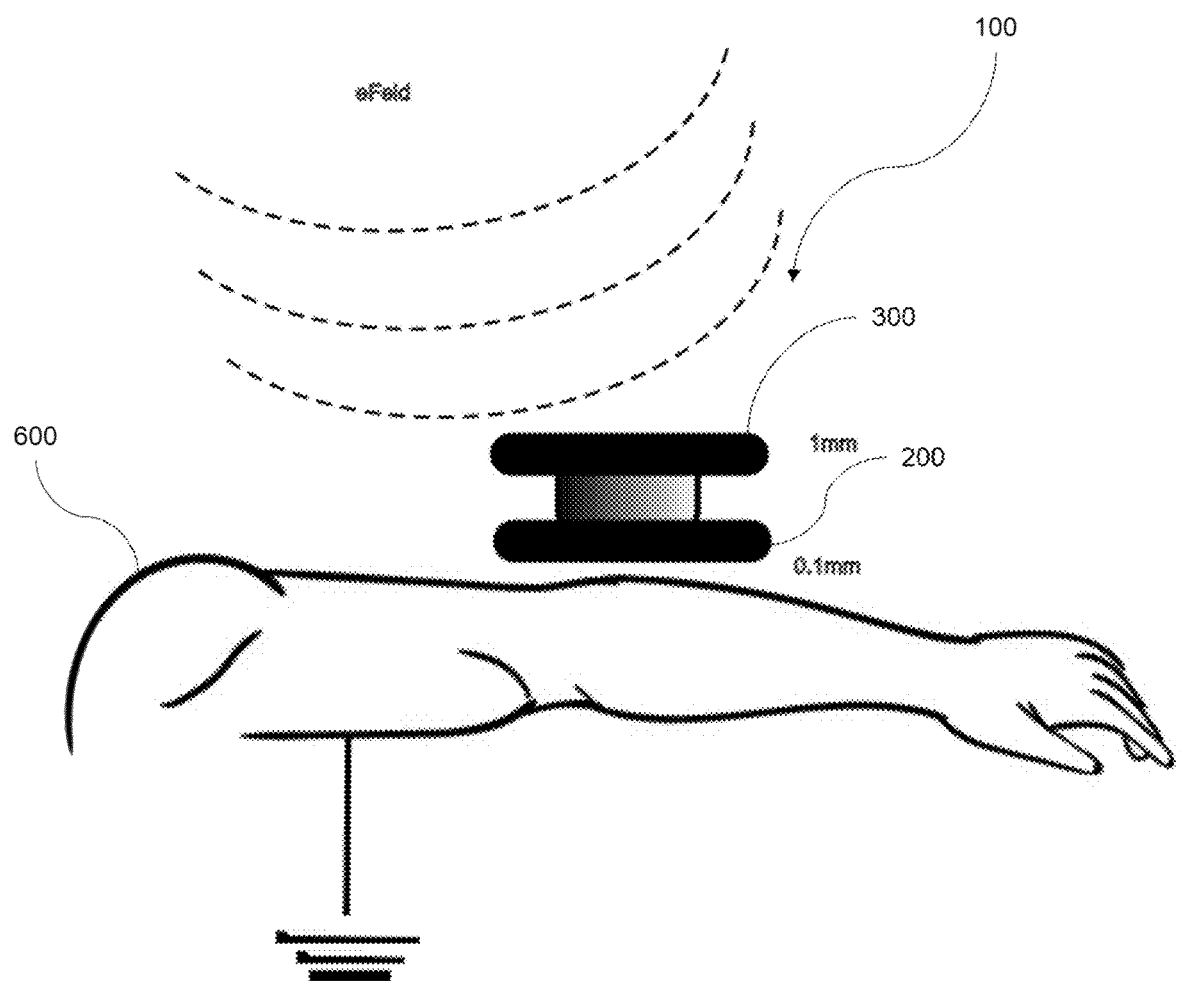
FIG. 7 shows a schematic view of the apparatus attached to a user in an exemplary embodiment of the present invention.

FIG. 7 shows a schematic view of the apparatus 100 attached to a user 600 in an exemplary embodiment of the present invention. The apparatus 100 measures vital signs of the user 600 under the influence of alternating electric field provided by an electronic device. The second electronic circuitry 300 is stacked on top of the first electronic circuitry 200 to create a delta ratio. In an exemplary embodiment, the distance of the user 600 from the first electronic circuitry 200 is 0.1 mm and the distance of the user 600 from the second electronic circuitry 300 is 1 mm. The stacking arrangement creates a voltage difference delta e.g. 5V, to power and operate the first electronic circuitry 200 and the second electronic circuitry 300 from the alternating electric field.

Further, the apparatus 100 also may detect movements and changes in the seating position of the person. It is further of importance to mention that the provided unique identifier number (ID) also propagates over the person (P), which means that actions of the person, for example, touching items or operating the car or a machine may be identified with another similar embodiment of the apparatus attached to the operated item or machine part.

This is useful for identifying or analyzing the dynamic of action in combination with the person's vital signals. For example, measuring or assessing the ability of the driver to operate a car (or a machine) over a time period. The apparatus 100 may also have means to output signals in the form of illumination (LED) or acoustic signals utilizing the piezo coating or control (electromechanical) actors. The received frequency also may be changed inside the apparatus e.g. by using a PLL to operate at higher- or a divider for lower rates than the frequency of the alternating electric field (F) or emit data as modulated radio waves under the control of the controller.

In another special arrangement, the alternating electric field may be swept in its frequency (e.g. from 10 kHz to 10 Mhz). The apparatus 100 would be able to measure bio-impedance, bio-resonance, body mass index (BMI), bladder level, etc. The analog/digital converting logic circuit 500 performs impedance spectroscopic analysis from the alternating electric field sweeps to measure bio-resonance.

Additional, or alternatively or to the piezo rings, similar pressure-sensitive (or electrodynamic) materials may be applied to the electrode, for example, but not limited to FSR, capacitive or resistive pressure sensors, MEMS, optical (fibres) diffraction, etc. If the apparatus 100 has a line of sight to the user, an IR Thermometer may also be attached to and operated by the apparatus 100 pointing to the user to measure the body temperature.

Exemplary Embodiments of the Invention

A mat for fitness, sport, yoga may be charged with the invention as described in FIG. 3. The person sitting, lying or acting on the mat is recognized e.g. to activate personalized training programs. Further, the present invention may be used on similar mats/mattresses to monitor babies, elders, or patients of a hospital. Push-ups on such mats may be checked for accuracy e.g. cardio training.

The apparatus may be placed on specified locations in a vehicle to get charged and measure vital or mental states of drivers, pilots, passengers, etc. for the purpose of comfort or safety. The apparatus may alert a parent/guardian when Infants or pets are left in overheating cars.

Various services may rely on the apparatus data to provide related service. It would be readily apparent to those skilled in the art that various types of applications may be envisioned without deviating from the scope of the present invention. There has thus been outlined, rather broadly, the more important features of the disclosure in order that the detailed description thereof may be better understood, and in order that the present contribution to the art may be better appreciated. There are additional features of the disclosure that will be described hereinafter and which will also form the subject matter of the claims appended hereto.

The features listed herein and other features, aspects and advantages of the present disclosure will become better understood with reference to the following description and appended claims. Indeed, it will be apparent to one of skill in the art how alternative functional configurations can be implemented to implement the desired features of the present disclosure. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present invention should not be limited by any of the above-described exemplary embodiments.

The invention claimed is:

1. An apparatus for measuring vital signs of a user, wherein the apparatus and the user are influenced by an alternating electric field provided by an electronic device, the apparatus comprising:
   a first electronic circuitry comprising:
      a first electrode configured to receive vital signals from the user's body;
      a first shield unit configured to shield the first electrode from electrical influences,
      wherein the first shield unit is influenced by the alternating electric field provided by the electronic device;
      a first rectifier configured to harvest and rectify the received alternating electric field from the first shield unit and provide DC energy;
      a first buffer configured to store the DC energy received from the first rectifier and provide differential voltages; and
      a first programmable operational amplifier configured to amplify the amplitude of the vital signals received via the first electrode, wherein the first programmable operational amplifier is powered by the differential voltage from the first buffer;
   a second electronic circuitry stacked on top of the first electronic circuitry to create a delta ratio of the received vital signals, the second electronic circuitry comprising:
      a second electrode configured to receive the vital signals from the user's body;
      a second shield unit configured to shield the second electrode from electrical influences, wherein the second shield unit is influenced by the alternating electric field provided by the electronic device;

a second rectifier configured to harvest and rectify the received alternating electric field from the second shield unit and provide DC energy;

a second buffer configured to store the DC energy received from the second rectifier and provide differential voltages; and a second programmable operational amplifier configured to amplify the amplitude of the vital signals received via the second electrode, wherein the second programmable operational amplifier is powered by the differential voltage from the second buffer;

an instrumentation amplifier configured to receive the amplified vital signals from the first programmable operational amplifier and the secondprogrammable operational amplifier, suppress the electrical influence, and create an amplified analog value representing the vital signs from the delta ratio between the first programmable operational amplifier and the second programmable operational amplifier;

an analog/digital converting logic circuit configured to generate digitized information from the amplified analog value representing the vital signs received from the instrumentation amplifier; and a communication unit configured to communicate the digitized information received from the analog/digital converting logic circuit over a communication network.

2. The apparatus according to claim 1, wherein the first electronic circuitry further comprises a first electronic switch configured to discharge static charges; and the second electronic circuitry further comprises a second electronic switch configured to discharge static charges.

3. The apparatus according to claim 1, wherein the first electronic circuitry further comprises a first impedance filter configured to filter vital signs from the vital signals received via the first electrode; and the second electronic circuitry further comprises a second impedance filter configured to filter vital signs from the vital signals received via the second electrode.

4. The apparatus according to claim 1, wherein the first electronic circuitry further comprises a first shield driver configured to drive the vital signs back to the first shield unit and cancel influential noise; and the second electronic circuitry further comprises a second shield driver configured to drive the vital signs back to the second shield unit and cancel the influential noise.

5. The apparatus according to claim 1, wherein the first electrode and the second electrode comprise a piezo coating for receiving electrical, mechanical, and acoustic signals from the user.

6. The apparatus according to claim 1, wherein the analog/digital converting logic circuit is configured to perform impedance spectroscopic analysis.

7. The apparatus according to claim 1, wherein the first electronic circuitry and the second electronic circuitry are configured as an implantable or with a medical device.

8. The apparatus according to claim 1, wherein the first electronic circuitry and the second electronic circuitry are configured within a catheter.

9. The apparatus according to claim 1, wherein the first electronic circuitry and the second electronic circuitry are configured within a thermometer.

10. The apparatus according to claim 1, wherein the analog/digital converting logic circuit further comprises a unique identification number configured to identify the user, and is configured to propagate the unique identification number to the electronic device over the user's body via capacitive coupling.

11. An apparatus for measuring vital signs of a user, the apparatus comprising:

an electronic device configured to generate an alternating electric field for influencing the user;

a first electronic circuitry comprising:
 a first electrode configured to receive vital signals provided by the user's body;
 a first shield unit configured to shield the first electrode from electrical influences, wherein the first shield unit is influenced by the alternating electric field provided by the electronic device;
 a first rectifier configured to harvest and rectify the received alternating electric field from the first shield unit and provide DC energy;
 a first buffer configured to store for the DC energy received from the first rectifier and provide differential voltages;
 a first programmable operational amplifier configured to amplify the amplitude of the vital signals received via the first electrode, wherein the first programmable operational amplifier is powered by the differential voltage from the first buffer;
 a first electronic switch configured to discharge static charges;
 a first impedance filter configured to filter vital signs from the vital signals received via the first electrode; and
 a first shield driver configured to drive the vital signs back to the first shield unit and cancel influential noise;

a second electronic circuitry stacked on top of the first electronic circuitry to create a delta ratio of the received vital signs, the second electronic circuitry comprising
 a second electrode configured to receive the vital signals from the user's body;
 a second shield unit configured to shield the second electrode from electrical influences, wherein the second shield unit is influenced by the alternating electric field provided by the electronic device;
 a second rectifier configured to harvest and rectify the received alternating electric field from the second shield unit and provide DC energy;
 a second buffer configured to store the DC energy received from the second rectifier and provide differential voltages;
 a second programmable operational amplifier configured to amplify the amplitude of the vital signals received via the second electrode, wherein the second programmable operational amplifier is powered by the differential voltage from the second buffer;
 a second electronic switch configured to discharge static charges;
 a second impedance filter configured to filter vital signs from the vital signals received via the second electrode; and
 a second shield driver configured to drive the vital signs back to the second shield unit and cancel influential noise;

an instrumentation amplifier configured to receive the amplified vital signals from the first programmable operational amplifier and the second programmable operational amplifier, suppress the electrical influence, and create an amplified analog value representing the vital signs from the delta ratio between the first programmable operational amplifier and the second programmable operational amplifier; and an analog/digital converting logic circuit configured to generate digitized information from the amplified analog value representing the vital signs received from the instrumentation amplifier; and modulate the impedance of the first impedance filter, the second impedance filter, the first shield driver and the second shield driver with the digitized information via the first electronic switch and the second electronic switch, wherein the modulated digitized information propagates to the electronic device via the alternating electric field, and wherein the electronic device is configured to convert the resulting changes in the impedance of the alternating electric field to values representing the vital signs.

12. The apparatus according to claim 11, wherein the first electrode and the second electrode comprise a piezo coating for receiving electrical, mechanical, and acoustic signals from the user.

13. The apparatus according to claim 11, further comprising a communication unit configured to communicate the digitalized information received from the analog/digital converting logic circuit over a communication network.

14. The apparatus according to claim 11, wherein the analog/digital converting logic circuit is configured to perform impedance spectroscopic analysis.

15. The apparatus according to claim 11, wherein the first electronic circuitry and the second electronic circuitry are configured as an implantable or with a medical device.

16. The apparatus according to claim 11, wherein the first electronic circuitry and the second electronic circuitry are configured within a catheter.

17. The apparatus according to claim 11, wherein the first electronic circuitry and the second electronic circuitry are configured within a thermometer.

* * * * *